United States Patent
Hui et al.

(10) Patent No.: US 10,028,704 B2
(45) Date of Patent: Jul. 24, 2018

(54) EXCHANGE GUIDEWIRE

(71) Applicant: THE CLEVELAND CLINIC FOUNDATION, Cleveland, OH (US)

(72) Inventors: Ferdinand Hui, Cleveland, OH (US); Shengqiang Gao, Beachwood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 133 days.

(21) Appl. No.: 14/200,078

(22) Filed: Mar. 7, 2014

(65) Prior Publication Data
US 2014/0257138 A1 Sep. 11, 2014

Related U.S. Application Data

(60) Provisional application No. 61/774,921, filed on Mar. 8, 2013.

(51) Int. Cl.
*A61B 5/00* (2006.01)
*A61M 25/01* (2006.01)
(Continued)

(52) U.S. Cl.
CPC ....... *A61B 5/6851* (2013.01); *A61M 25/0169* (2013.01); *A61M 25/09* (2013.01);
(Continued)

(58) Field of Classification Search
CPC ............ A61M 25/09; A61M 25/09033; A61M 25/09066; A61M 25/09083;
(Continued)

(56) References Cited

U.S. PATENT DOCUMENTS 6,132,388 A * 10/2000 Fleming ................ A61M 25/09
600/585
6,251,084 B1 * 6/2001 Coelho ............. A61M 25/0102
606/194
(Continued)

FOREIGN PATENT DOCUMENTS

EP 1642540 A1 4/2006
EP 2260898 A1 12/2010
(Continued)

OTHER PUBLICATIONS

International Search Report and Written Opinion for PCT/US2014/021491, dated Jul. 4, 2014, pp. 1-15.

*Primary Examiner* — Jeffrey G Hoekstra
*Assistant Examiner* — Yasmeen S Warsi
(74) *Attorney, Agent, or Firm* — Tarolli, Sundheim, Covell & Tummino LLP

(57) ABSTRACT

A guidewire (10) includes a flexible elongated core (20) having a proximal end (22) and a distal end (24). An anchor wire (10) has a distal end (34) connected to the distal end (24) of the core (20) and a distally located helical portion (50) that encircles the core. The guidewire (10) has an anchoring condition in which the helical portion (50) is expanded radially away from the core (20). The guidewire (10) has an advancing condition in which the helical portion (50) is stretched longitudinally and contracted radially in response to tension on the anchor wire (30).

13 Claims, 4 Drawing Sheets

(51) Int. Cl.
    *A61M 25/09*      (2006.01)
    *A61B 17/22*      (2006.01)
    *A61M 25/04*      (2006.01)

(52) U.S. Cl.
    CPC .... *A61B 2017/22047* (2013.01); *A61M 25/04* (2013.01); *A61M 2025/09125* (2013.01); *A61M 2025/09191* (2013.01)

(58) Field of Classification Search
    CPC ...... A61M 25/09091; A61M 25/09141; A61M 25/09191; A61B 5/6851
    See application file for complete search history.

(56) References Cited

U.S. PATENT DOCUMENTS

| | | | |
|---|---|---|---|
| 8,062,284 B2 | 11/2011 | Booth | |
| 2002/0004644 A1* | 1/2002 | Koblish | A61B 18/1492 604/104 |
| 2005/0182437 A1* | 8/2005 | Bonnette | A61M 25/09033 606/194 |
| 2006/0195137 A1 | 8/2006 | Sepetka et al. | |
| 2009/0171293 A1 | 7/2009 | Yang et al. | |
| 2012/0172844 A1 | 7/2012 | Mullen | |

FOREIGN PATENT DOCUMENTS

| | | |
|---|---|---|
| GB | 2469072 A | 3/2009 |
| WO | 0126725 A1 | 4/2001 |
| WO | 2009140209 A1 | 11/2009 |
| WO | 2010119445 A1 | 10/2010 |

* cited by examiner

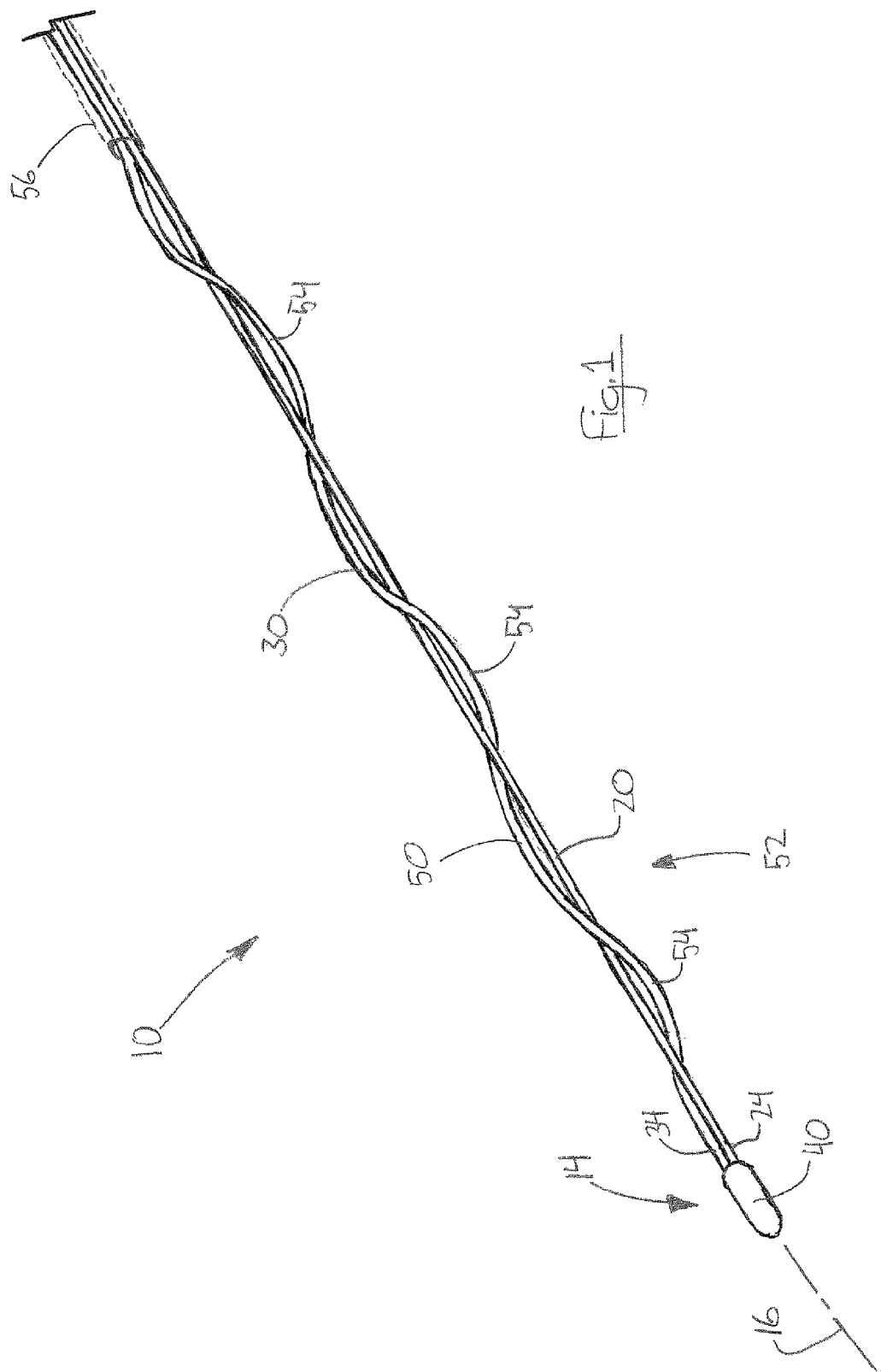

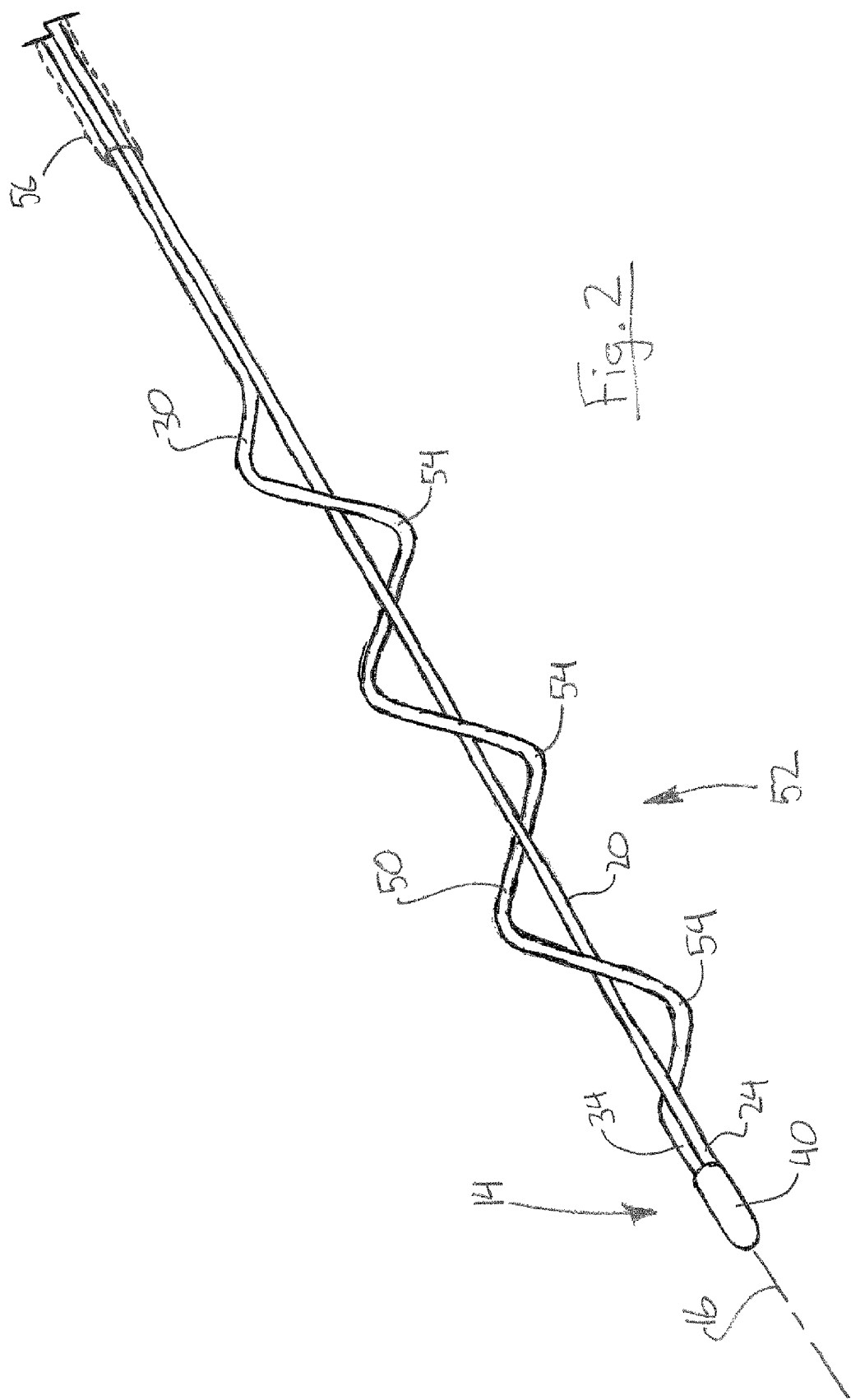

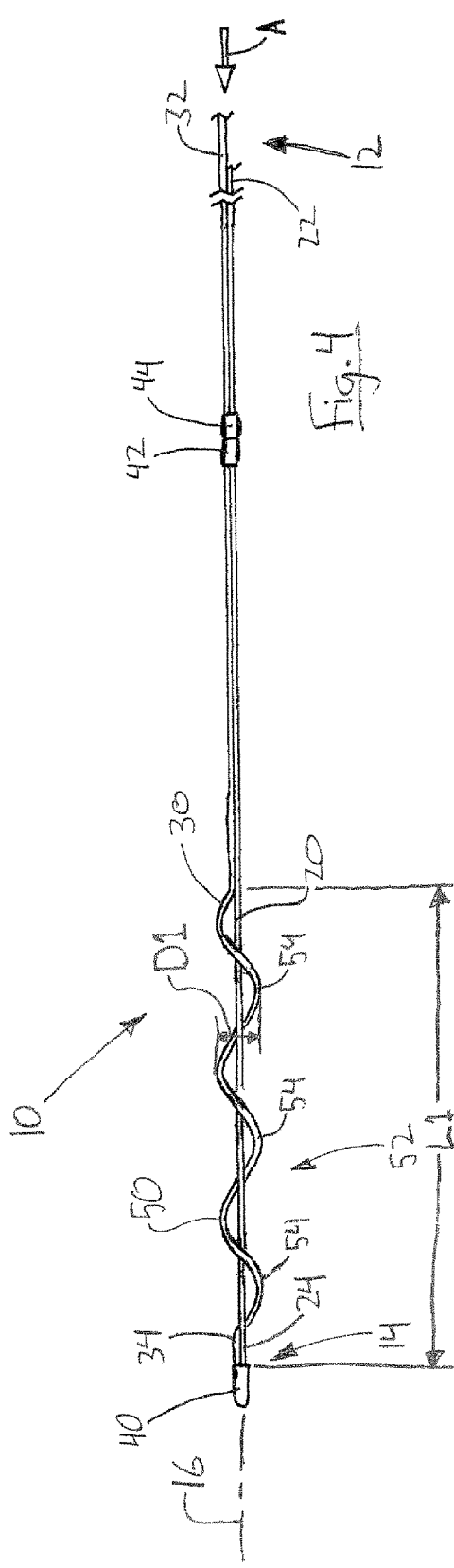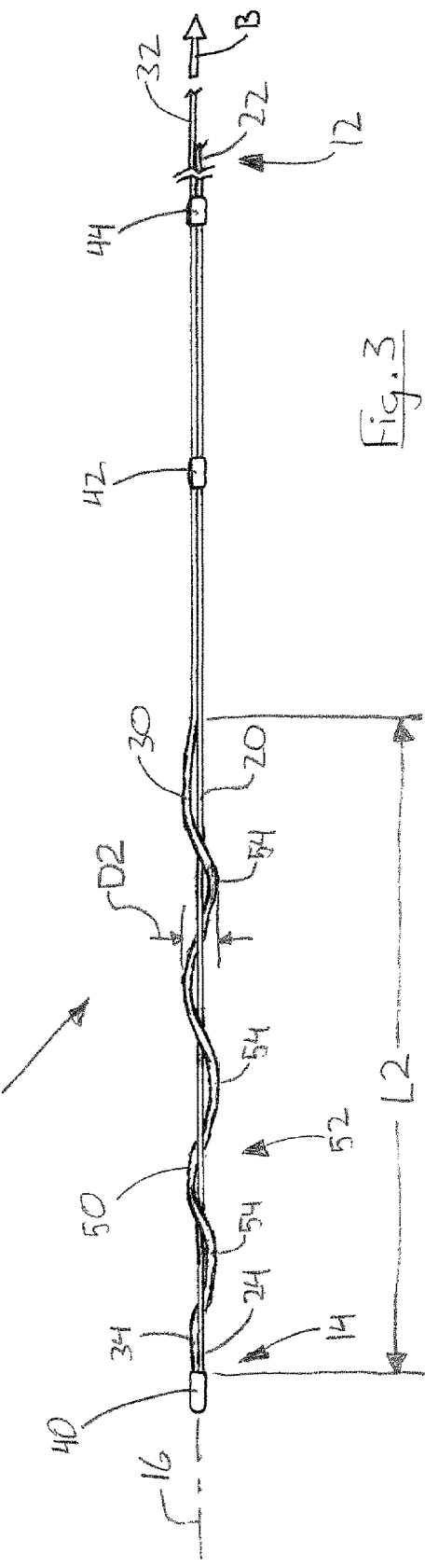

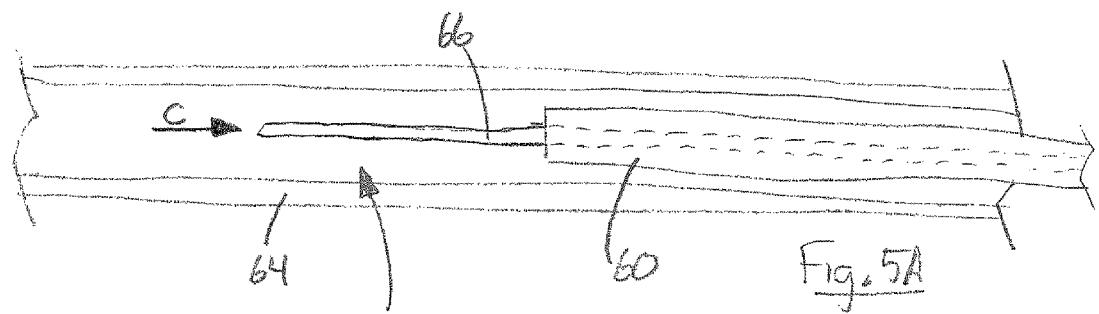
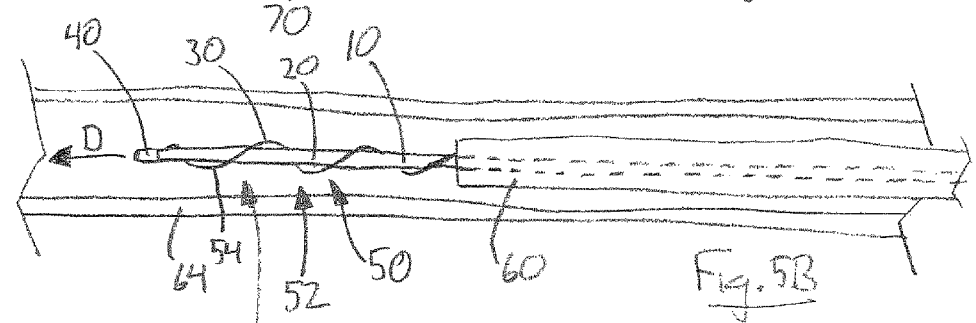
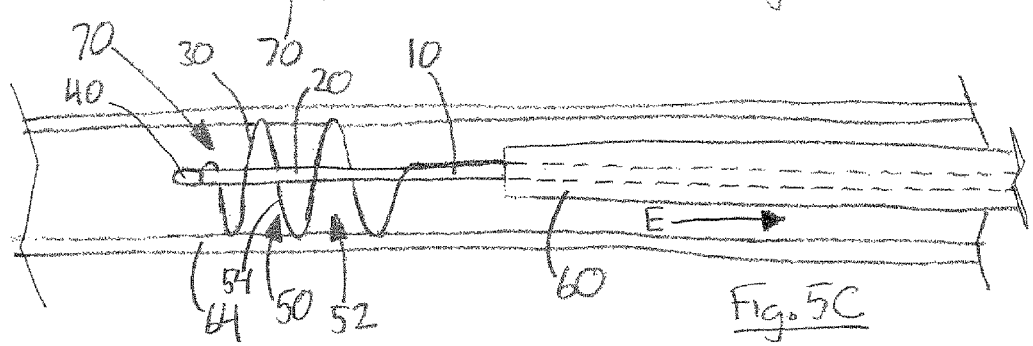
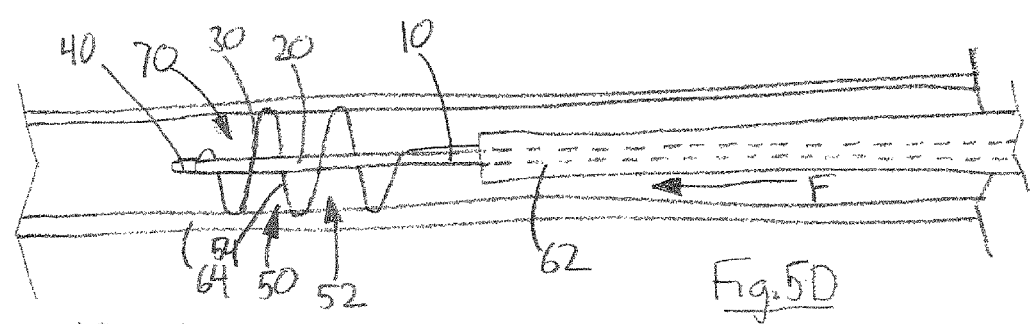
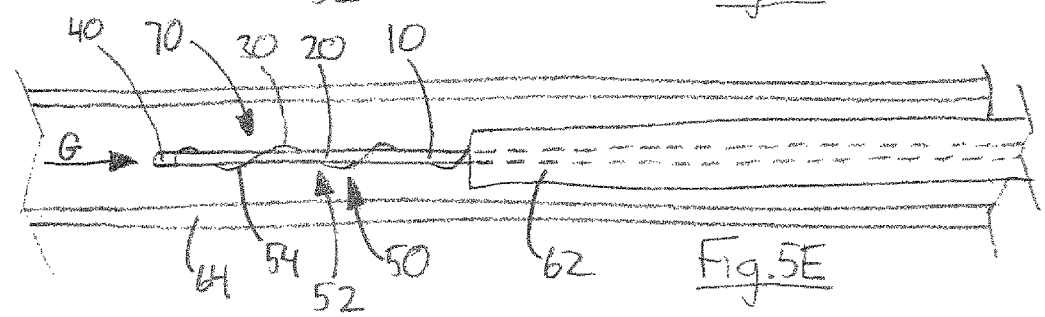

EXCHANGE GUIDEWIRE

CROSS-REFERENCE TO RELATED APPLICATION

This application claims the benefit of U.S. Provisional application No. 61/774,921, filed Mar. 8, 2013, and entitled EXCHANGE GUIDEWIRE, the entire contents of which are incorporated herein by reference.

TECHNICAL FIELD

The invention relates generally to a guidewire for interventional and diagnostic use in the vascular system. More particularly, the invention relates to an exchange guidewire having a distal end portion with an actuatable anchor for stabilizing the guidewire in a vessel.

BACKGROUND OF THE INVENTION

The vascular field of medicine relates to the diagnosis, management and treatment of diseases affecting the arteries and veins. Even when healthy, the anatomy of these vessels is complex, with numerous divisions leading into progressively smaller branches. Development of disease within these vessels often complicates matters by altering their caliber, flexibility, and direction. The interior, or lumen, of a blood vessel may develop constrictions, known as stenoses, and at times may even be obstructed, as a result of the development of atherosclerotic plaques or by the occurrence of tears or lacerations in the vessel wall, known as dissections. These obstructions may complicate the vascular anatomy by leading to the formation of new collateral pathways that establish new routes around the obstructions in order to provide blood flow down-stream from the blockage.

In order to diagnose and treat vascular diseases, a physician may in many instances perform a diagnostic or interventional angiogram. An angiogram is a specialized form of X-ray imaging, requiring physical access into a vessel with some form of sheath, needle or guide in order to allow a contrast dye to be injected into the vasculature while X-rays are transmitted through the tissue to obtain an image. The contrast dye illuminates the interior of the vessels and allows the physician to observe the anatomy, as well as any narrowings, abnormalities or blockages within the vessels. At times, more selective angiograms are used to delineate a particular area of concern or disease with greater clarity. Access to these more selective areas often requires the insertion of guidewires into the vessels.

Vascular guidewires can be visualized from outside the body, even as they are manipulated through the body's vascular system, through the use of continuous low-dose fluoroscopy. The negotiation of the complex vascular anatomy, even when healthy, can be difficult and time consuming. When narrowed or obstructed by disease, the vessels can be even more difficult, if not impossible, to negotiate. To account for this difficulty, many specialized guidewire and catheter systems have been developed to negotiate difficult vessel pathways in order to reach the treatment site.

Once guidewire reaches the treatment site, a catheter is installed over the guidewire, and the guidewire steers the catheter to the treatment site. The catheter is specially equipped to perform a desired specialized function, such as balloon angioplasty or stent delivery and/or dilation. In performing these procedures, it is often necessary to use multiple different catheters to perform various different functions. A guidewire is required to facilitate these catheter exchanges. Often, however, the guidewire can shift positions during catheter exchange procedures, advancing further into the vessel or backing out of the vessel. This tendency of the guidewire to move or "migrate" during catheter exchange procedures is undesirable.

SUMMARY OF THE INVENTION

The invention relates to a guidewire that includes a flexible elongated core having a proximal end and a distal end. The guidewire also includes an anchor wire that has a distal end connected to the distal end of the core and a distally located helical portion that encircles the core. The guidewire has an anchoring condition in which the helical portion is expanded radially away from the core. The guidewire has an advancing condition in which the helical portion is stretched longitudinally and contracted radially in response to tension on the anchor wire.

BRIEF DESCRIPTION OF THE DRAWINGS

For a better understanding of the invention, reference may be made to the accompanying drawings, in which:

FIG. 1 is a perspective view of a portion of a guidewire in a first condition, according to the invention;

FIG. 2 is a perspective view of a portion of the guidewire of FIG. 1 in a second condition;

FIG. 3 is a plan view of the guidewire of FIG. 1;

FIG. 4 is a plan view of the guidewire of FIG. 2; and

FIGS. 5A-5E are schematic views illustrating the guidewire during use.

DETAILED DESCRIPTION

The invention relates to an apparatus 10 in the form of an exchange guidewire for facilitating installation and removal of a catheter. The guidewire 10 is illustrated in FIGS. 1-4. The guidewire 10 has longitudinally spaced proximal and distal ends 12 and 14, respectively. The term "longitudinal" is used herein to refer to a direction defined by the length of the guidewire 10, which is substantially horizontal in the orientation of FIGS. 3 and 4, extending along a central axis 16 of the guidewire 10. The term "lateral" is used herein to refer to a direction which is transverse to the longitudinal direction, i.e., transverse to the guidewire axis 16. The term "radial" is used herein to refer to a direction which is radial with respect to the longitudinal direction, i.e., radial with respect to the guidewire axis 16.

The guidewire 10 includes a flexible elongated core 20 that has a proximal end 22 and a distal end 24. The guidewire 10 also includes a flexible elongated anchor wire 30 that has a proximal end 32 and a distal end 34. The guidewire 10 also includes a tip 40 secured to the distal end 24 of the core 20 and the distal end 34 of the anchor wire 30. The tip 40 thus interconnects the distal ends 24, 34 of the core 20 and anchor wire 30, respectively. The interconnection of the core 20, anchor wire 30, and tip 40 is achieved by known means, such as adhesives or soldering. The tip 40 defines the distal end 14 of the guidewire 10.

The core 20 and the anchor wire 30 may be wrapped in a protective sheath 56, shown in FIGS. 1 and 2, that maintains the relative positions of the core and anchor wire so that they are coextensive with the axis 16. The sheath 56 permits relative axial movement between the anchor wire 30 and the core 20.

A first marker 42 is secured to the core 20 and movable with the core. The anchor wire 30 extends through the first marker 42 and is movable longitudinally through the first marker. The first marker 42 thus permits the anchor wire 30 to move longitudinally relative to the core 20. A second marker 44 is secured to the anchor wire 30 and movable with the anchor wire. The core 20 extends through the second marker 44 and is movable longitudinally through the second marker. The second marker 44 is thus movable longitudinally over the core 20 and with the anchor wire 30.

The core 20 is constructed of a material, such as stainless steel (e.g., a 304 surgical grade stainless steel), and has a diameter selected to facilitate its use as a vascular guidewire. For example, the core 20 may have a diameter of about 0.34 mm. The anchor wire 30 can be constructed of a material, such as a nickel-titanium ("nitinol") alloy, that has relatively high elasticity and shape memory properties. The anchor wire 30 may have a comparatively small diameter, such as about 0.12 mm. The tip 40, first marker 42, and second marker 44 can be constructed of a radiopaque material, such as gold, platinum, iridium or a combination thereof, such as a platinum-iridium alloy. The tip 40 and markers 42, 44 therefore can be viewed on x-rays.

The anchor wire 30 includes a helical portion 50 adjacent the tip 40 that defines a distally located anchoring section 52 of the guidewire 10. The helical portion 50 is a portion of the anchor wire 30 that is wound in the form of a coil or helix in a manner similar or identical to that of a coil spring. The helical portion 50 extends generally along the axis 16 of the guidewire 10. The helical portion has a length measured longitudinally along the axis 16 and a diameter measured radially from the axis. In the illustrated embodiment, the helical portion 50 includes about three individual helical coils or windings 54. The helical portion 50 could, however, include a greater or lesser number of coils 54.

The length and diameter of the helical portion 50 can vary in proportion to the degree to which the helical portion is deformed or stretched longitudinally along the axis 16. Tension applied to the helical portion 50 causes it to stretch and deform longitudinally. As a result, the length of the helical portion 50 increases and the diameter of the helical portion decreases. When the tension is relieved, the elastic properties of the helical portion 50 causes it to resume its non-tensioned form. As a result, the length of the helical portion 50 decreases and the diameter of the helical portion increases.

Because the anchor wire 30 is constructed of a material exhibiting high elasticity and shape memory properties, e.g., nitinol, the helical portion 50 possesses a high tendency to maintain its spring properties. Thus, when the anchor wire 30 is tensioned causing the helical portion 50 to stretch longitudinally, it has a high tendency to reassume its original helical form once that tension is relieved. The helical portion 50 thus may have a non-tensioned length and diameter to which it will consistently and reliably return to after having been deformed due to tension on the anchor wire 30.

The differences in material construction and the configuration (e.g., diameter) of the core 20 versus the anchor wire 30 are selected such that the core has physical characteristics, such as rigidity or stiffness, that permit the helical portion 50 to be stretched longitudinally by applying a tension force to the anchor wire while maintaining the longitudinal position of the core. In other words, the helical portion 50 can be stretched longitudinally by pulling or otherwise moving the anchor wire 30 axially relative to the core 20 in the direction indicated generally at B in FIG. 3. Conversely, this longitudinal stretching can be relieved by pushing or otherwise moving the anchor wire 30 axially relative to the core 20 in the direction indicated generally at A in FIG. 4.

The guidewire 10 has an advancing condition, illustrated in FIGS. 1 and 3, and an anchoring condition, illustrated in FIGS. 2 and 4. In the advancing condition, the helical portion 50 is stretched longitudinally by pulling the anchor wire 30 relative to the core 20 in direction B (see FIG. 3). When stretched in this manner, the length of the helical portion 50 increases, as indicated generally at L2 in FIG. 3, and the coil diameter decreases, as indicated generally at D2 in FIG. 3. In the anchoring condition, the longitudinal stretch of the helical portion 50 is relieved by pushing the anchor wire 30 relative to the core 20 in direction A (see FIG. 4). When the longitudinal stretch is relieved, the length of the helical portion 50 decreases, as indicated generally at L1 in FIG. 4, and the coil diameter increases, as indicated generally at D1 in FIG. 4.

The length and diameter of the helical portion 50 can be controlled by selecting the appropriate amount of linear or longitudinal displacement of the anchor wire 30 relative to the core 20. The markers 42, 44, being fixed to the core 20 and anchor wire 30, respectively, act as stop pieces that limit movement of the anchor wire relative to the core in direction A. The markers 42, 44 thus define the maximum diameter of the helical portion 50. The relative positions of the markers 42, 44 can be adjusted so that the diameter D1 defined by the stop points is of a desired size in the anchoring condition. In fact, in one embodiment, the relative positions of the markers 42, 44 could even be adjustable by the operating physician so that predetermined stop points, resulting in predetermined anchoring diameters, can be selected.

Referring to FIGS. 5A-5E, in operation, the guidewire 10 is used to facilitate an in situ catheter exchange, replacing a first catheter 60 already positioned in the patient's vasculature 64 with a second catheter 62. For example, it may be necessary to exchange a balloon angioplasty catheter with a stent delivery catheter. In this scenario, as shown in FIG. 5A, a steerable guidewire 66 is used initially to deliver or guide the first catheter 60 through the vasculature 64 to the worksite 70 in the patient. The guidewire 66 is then removed, as indicated generally by arrow C in FIG. 5A.

Once the procedure(s) performed via the first catheter 60 are complete, the exchange guidewire 10 is placed in the advancing condition of FIGS. 1 and 3, and advanced through the first catheter, as indicated generally by arrow D in FIG. 5B. The guidewire 10 is advanced such that the anchoring section 52 is positioned at a desired location in the vasculature 64, e.g., at or near the worksite 70. Throughout the procedure, the position of the guidewire 10 can be ascertained by monitoring the position of the tip 40 and markers 42, 44 (see FIGS. 1-4) via x-ray.

Once the anchoring section 52 reaches the desired location, the operating physician manipulates the guidewire from the proximal end 12 to move the anchor wire 30 in the direction A (see FIGS. 2 and 4), while maintaining the position of the core 20 to place the guidewire 10 in the anchoring position, as shown in FIG. 5C. The position of the guidewire 10 can be monitored and maintained via x-ray to ensure that the anchoring section 52 is maintained in the proper position while the helical portion 50 expands radially. In the anchoring position, the diameter of the helical portion 50 increases (see D1, FIG. 4) such that the coils 54 engage the vascular wall. The operating physician can monitor the diameter of the helical portion 50 by monitoring the relative positions of the markers 42, 44. The anchoring section 52 thereby anchors the guidewire 10 in the vasculature 64, which allows for removal of the first catheter 60, as indicated generally by arrow E in FIG. 5C, without affecting the positioning of the guidewire.

Once the first catheter 60 is removed, the second catheter 62 can be advanced over the guidewire 10, as indicated generally by arrow F in FIG. 5D, to a working position in the vasculature 64. While the second catheter 62 is being advanced, the guidewire 10 is maintained in the anchoring condition, as shown in FIG. 5D. This helps to ensure that the second catheter 62 can be delivered to the worksite 70 in a repeatable and reliable manner.

Once the second catheter 62 reaches the worksite 70 in the vasculature 64, the operating physician manipulates the guidewire from the proximal end 12 to move the anchor wire 30 in the direction B (see FIGS. 1 and 3), while maintaining the position of the core 20 to place the guidewire 10 in the advancing position, as shown in FIG. 5F. Again, the position of the guidewire 10 can be monitored and maintained via x-ray to ensure that the anchoring section 52 is maintained in the proper position while the helical portion 50 contracts radially. In the advancing position, the diameter of the helical portion 50 decreases (see D2, FIG. 3) such that the coils 54 disengage from the vascular wall. The anchoring section 52 thereby freed from the vasculature 64, which allows for removal of the guidewire 10, as indicated generally by arrow G in FIG. 5F, leaving the second catheter 62 at the desired position at the worksite 70.

From the above description of the invention, those skilled in the art will perceive improvements, changes and modifications. Such improvements, changes and modifications within the skill of the art are intended to be covered by the appended claims.

Having described the invention, we claim:

1. An apparatus comprising:
    a first catheter configured to be advanced through vasculature to a surgical site;
    a second catheter configured to be advanced through vasculature to a surgical site; and
    an exchange guidewire configured to be advanced through the first catheter in order to facilitate removal of the first catheter from the vasculature and to facilitate advancement of the second catheter over the exchange guidewire and through the vasculature to deliver the second catheter to the surgical site, the exchange guidewire comprising:
    a core having a flexible elongated construction and including proximal end and a distal end;
    an anchor wire having a distal end connected to the distal end of the core and an adjacent helical portion wound around the core;
    a first stop piece fixed to the core and through which the anchor wire extends, the first stop piece permitting the anchor wire to move axially relative to the core; and
    a second stop piece fixed to the anchor wire and through which the core extends, the second stop piece moving axially over the core in response to axial movement of the anchor wire relative to the core;
    wherein the exchange guidewire is configured to have an anchoring condition in which the helical portion is expanded radially away from the core in response axial movement of the anchor wire relative to the core toward the distal end of the core, and wherein the exchange guidewire is configured to have an advancing condition in which the helical portion is extended longitudinally and contracted radially toward the core in response to axial movement of the anchor wire relative to the core toward the proximal end of the core; and
    wherein the exchange guidewire is configured to be advanced through the first catheter to position the helical portion outside a distal end of the first catheter at the surgical site, the exchange guidewire being further configured to be placed in the anchoring condition to anchor the exchange guidewire at the surgical site to facilitate removal of the first catheter from the vasculature and advancement of the second catheter over the exchange guidewire through the vasculature to the surgical site to replace the first catheter.

2. The apparatus recited in claim 1, wherein the first and second stop pieces are configured to be spaced apart a predetermined distance when the guidewire is in the advancing condition, and wherein axial movement of the anchor wire relative to the core toward the anchoring condition is limited by the stop pieces engaging each other.

3. The apparatus recited in claim 2, wherein the predetermined distance that the first and second stop pieces are spaced apart is configured to govern the outside diameter of the helical portion when the guidewire is in the anchoring condition.

4. The apparatus recited in claim 1, wherein the position of at least one of the first and second stop pieces is adjustable to select the outside diameter of the helical portion when the guidewire is in the anchoring condition.

5. The apparatus recited in claim 1, wherein the first stop piece, being fixed to the core, moves with the core, and wherein the second stop piece, being fixed to the anchor wire, moves with the anchor wire.

6. The apparatus recited in claim 1, wherein the tension on the anchor wire is applied and relieved from the proximal end of the anchor wire.

7. The apparatus recited in claim 1, wherein the helical portion of the anchor wire is constructed of a material that resumes due to shape memory the anchoring condition after being deformed to the advancing condition.

8. The apparatus recited in claim 7, wherein the shape memory material comprises a Nickel-Titanium alloy.

9. The apparatus recited in claim 1, wherein the first and second stop pieces comprise markers constructed of a radiopaque material.

10. The apparatus recited in claim 1, further comprising a tip piece that secures the distal end of the anchor wire to the distal end of the core, the tip piece comprising a radiopaque material.

11. The apparatus recited in claim 1, further comprising a sheath that wraps portions of the core and anchor wire that extend proximally of the helical portion, the sheath permitting relative axial movement of the core and anchor wire.

12. The apparatus recited in claim 1, wherein the guidewire is configured to:
    be advanced through the first catheter while in the advancing condition until the helical portion of the anchor wire extends out from a distal tip of the first catheter;
    be placed in the anchoring condition while the helical portion is positioned outside the distal end of the catheter to anchor the guidewire while the first catheter is removed from the guidewire;
    remain anchored while the second catheter is installed onto the guidewire; and
    be placed in the advancing condition and removed from the second catheter, leaving the second catheter at the same position where the first catheter was positioned.

13. An apparatus comprising:
a first catheter configured to be delivered through vasculature to place a distal end of the first catheter at a desired position relative to a surgical site;
an exchange guidewire comprising:
a core having a flexible elongated construction and including proximal end and a distal end;
an anchor wire having a distal end connected to the distal end of the core and an adjacent helical portion wound around the core;
a first stop piece fixed to the core and through which the anchor wire extends, the first stop piece permitting the anchor wire to move axially relative to the core; and
a second stop piece fixed to the anchor wire and through which the core extends, the second stop piece moving axially over the core in response to axial movement of the anchor wire relative to the core;
the exchange guidewire having an advancing condition in which the helical portion is contracted radially and an anchoring condition in which the helical portion is expanded radially, the exchange guidewire being configured to be advanced through the first catheter while the helical portion is in the advancing condition to position the helical portion outside the distal end of the first catheter, the helical portion being actuatable to the anchoring condition while positioned outside the distal end of the first catheter to anchor the exchange guidewire and facilitate removal of the first catheter from the vasculature while leaving the exchange guidewire anchored in position in the vasculature; and
a second catheter configured to be advanced over the exchange guidewire through the vasculature toward the surgical site to replace the first catheter once the first catheter is removed, wherein the exchange guidewire is actuatable to the advancing condition to facilitate removal of the exchange guidewire from the second catheter and the vasculature and leave the second catheter at the desired position relative to the surgical site.

\* \* \* \* \*